(12) United States Patent
Sullivan (10) Patent No.: US 11,646,110 B2
(45) Date of Patent: May 9, 2023

(54) SYSTEM AND METHOD FOR IMPROVING THE EMOTIONAL MINDSET OF THE USER

(71) Applicant: Sean Sullivan, San Francisco, CA (US)

(72) Inventor: Sean Sullivan, San Francisco, CA (US)

( * ) Notice: Subject to any disclaimer, the term of this patent is extended or adjusted under 35 U.S.C. 154(b) by 445 days.

(21) Appl. No.: 16/562,196

(22) Filed: Sep. 5, 2019

(65) Prior Publication Data

US 2020/0303056 A1 Sep. 24, 2020

Related U.S. Application Data (60) Provisional application No. 62/820,998, filed on Mar. 20, 2019, provisional application No. 62/728,682, filed on Sep. 7, 2018.

(51) Int. Cl.
| | | |
|---|---|---|
| *G16H 20/70* | (2018.01) | |
| *G06F 3/01* | (2006.01) | |
| *G06T 19/00* | (2011.01) | |
| *A61B 5/00* | (2006.01) | |
| *A61N 1/36* | (2006.01) | |
| *G06V 20/20* | (2022.01) | |

(52) U.S. Cl.
CPC ............... *G16H 20/70* (2018.01); *A61B 5/74* (2013.01); *A61N 1/36092* (2013.01); *G06F 3/011* (2013.01); *G06T 19/006* (2013.01); *G06V 20/20* (2022.01)

(58) Field of Classification Search
None
See application file for complete search history.

(56) References Cited

U.S. PATENT DOCUMENTS

| | | | | |
|---|---|---|---|---|
| 8,862,581 | B2* | 10/2014 | Zhang | A61B 5/165 |
| | | | | 707/750 |
| 9,173,582 | B2* | 11/2015 | Popovic | A61B 5/389 |
| 9,336,268 | B1* | 5/2016 | Moudy | G06F 40/40 |
| 9,509,789 | B2* | 11/2016 | Cronin | H04L 67/32 |
| 9,566,411 | B1* | 2/2017 | Sherpa | G16H 50/20 |
| 10,252,058 | B1* | 4/2019 | Fuerst | A61B 5/165 |
| 10,365,716 | B2* | 7/2019 | Aimone | A61B 5/378 |
| 10,888,270 | B2* | 1/2021 | Abrahami | A61B 5/0205 |
| 10,901,509 | B2* | 1/2021 | Aimone | H04W 4/30 |
| 11,013,449 | B2* | 5/2021 | Sriram | A61B 5/165 |
| 11,071,496 | B2* | 7/2021 | Abrahami | A61B 5/486 |
| 2011/0260830 | A1* | 10/2011 | Weising | G06F 3/015 |
| | | | | 340/5.52 |
| 2011/0300847 | A1* | 12/2011 | Quy | A61B 5/02405 |
| | | | | 455/419 |
| 2013/0296987 | A1* | 11/2013 | Rogers | A61F 7/12 |
| | | | | 607/113 |

(Continued)

*Primary Examiner* — Shirley X Jian
(74) *Attorney, Agent, or Firm* — Avek IP, LLC (57) ABSTRACT

A system for improving an emotional mindset of a person, the system includes a server to receive and process data; a computing device in data communication with the server; one or more software rules implemented through the server and computing device; a platform implemented through the computing device, the platform to perform the steps of: receive a user identified need; a meditation packet created by the computing device, server, and one or more software rules, the meditation packet having resources complied based on the user identified need, the meditation packet to aid the user with the user identified need; the meditation packet is provided to the user through the platform.

16 Claims, 5 Drawing Sheets

(56) References Cited

U.S. PATENT DOCUMENTS

| | | | | |
|---|---|---|---|---|
| 2014/0318699 A1* | 10/2014 | Longinotti-Buitoni | ...................... H05K 1/038 156/247 |
| 2014/0347265 A1* | 11/2014 | Aimone | ................ H04W 4/029 345/156 |
| 2015/0351655 A1* | 12/2015 | Coleman | ................ G16H 50/20 600/301 |
| 2015/0358415 A1* | 12/2015 | Cronin | ................... G06Q 50/01 709/217 |
| 2016/0279435 A1* | 9/2016 | Hyde | .................... A61H 23/02 |
| 2017/0007165 A1* | 1/2017 | Jain | ..................... A61B 5/0205 |
| 2017/0019496 A1* | 1/2017 | Orbach | ................. H04L 67/306 |
| 2017/0039045 A1* | 2/2017 | Abrahami | .............. A61B 5/1118 |
| 2018/0193589 A1* | 7/2018 | McLaughlin | .......... G16H 50/30 |
| 2018/0365384 A1* | 12/2018 | Althoff | ................. A61B 5/7275 |
| 2019/0030277 A1* | 1/2019 | Espi Maques | ......... G09B 19/00 |
| 2019/0189259 A1* | 6/2019 | Clark | .................... G16H 10/60 |
| 2019/0269345 A1* | 9/2019 | Sriram | .................. A61M 21/02 |
| 2021/0165490 A1* | 6/2021 | Aimone | ................ G06F 3/0487 |

\* cited by examiner

SYSTEM AND METHOD FOR IMPROVING THE EMOTIONAL MINDSET OF THE USER

BACKGROUND

1. Field of the Invention

The present invention relates generally to mobile and computer applications, as well as virtual reality and augmented reality systems, and more specifically, to a system and method that can be implemented through computing devices, such as a virtual reality device, phone, or computer, that helps users improve their emotional state and overall wellbeing.

2. Description of Related Art

Figure 1:
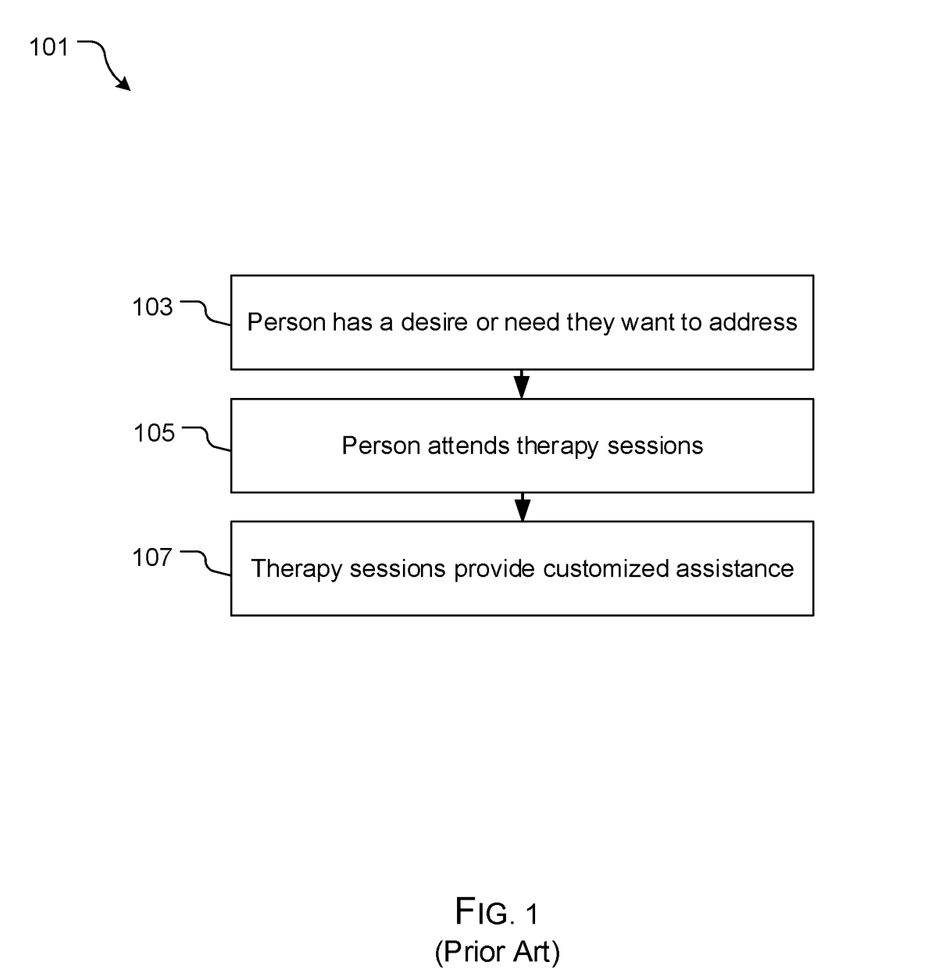
FIG. 1 is a flowchart of a conventional method of therapy for improving one's mental state.

Having the ability to improve one's emotional state or mood is an important and useful skill. This skill is not always easily developed, and many people do not take the time, or put in the effort, to develop such a skill. Conventional systems exist to aid individuals in this process. For example, FIG. 1 depicts a flowchart 101 of a conventional method, wherein a person has a desire or need that they want to improve, as shown with box 103. This desire or need could be an emotional or mental struggle, such as anxiety, depression, grief, or the like. The person may attend in person therapy sessions wherein they receive customized assistance, as shown with boxes 105, 107. This system and method can be effective to help the person improve their mental state, however, many individuals will not take the time and effort to consistently go to in person therapy. Further, there are some online style therapy sessions, however, they are lacking in customization and personalization, thereby limiting their effectiveness.

Accordingly, it is desirable, and an object of the present application to provide a system and method that allows users to improve their emotional state from their home (or other suitable environment) and on their own time. Having a system and method that is easy for users to utilize, is fun and enjoyable, and non-time consuming, can help many people fit in emotional training within their busy schedules.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The system and method of use in accordance with the present application overcomes one or more of the above-discussed problems commonly associated with conventional therapy and emotional improvement systems. Specifically, the present invention provides for a meditation system that includes a crowd sourcing function to create meditation packets that provide quality solutions and helpful insights to a user through implementation of artificial intelligence algorithms. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
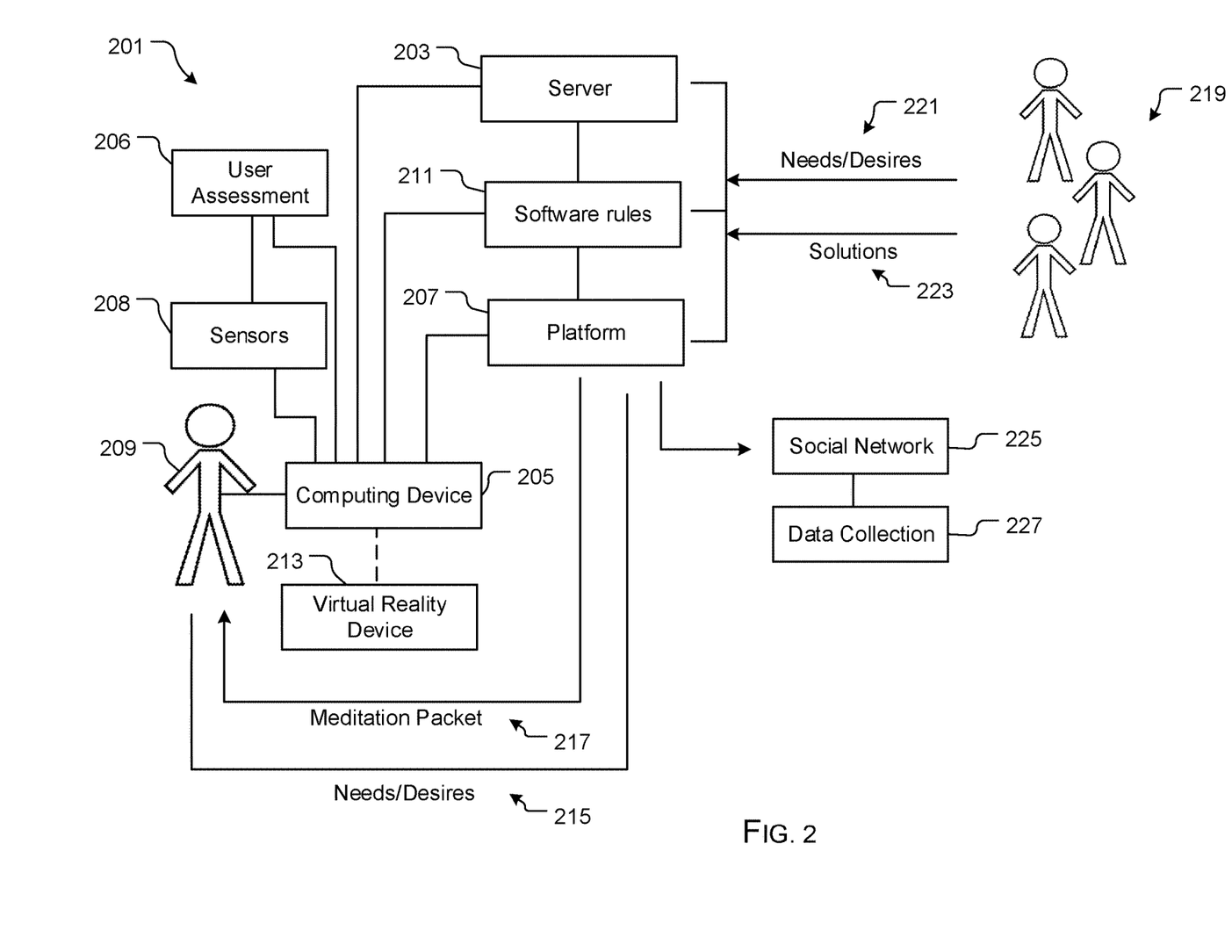
FIG. 2 is a schematic of a system for improving the emotional mindset of a user in accordance with a preferred embodiment of the present application.

Referring now to the drawings wherein like reference characters identify corresponding or similar elements throughout the several views, FIG. 2 depicts a schematic of a system 201 for improving an emotional mindset of a person in accordance with a present invention. System 201 includes a server 203 configured to receive and process data, the server in data communication with a computing device 205, and a platform 207 configured to receive and implement a user's 209 preference. System 201 further includes one or more software rules 211, such as artificial intelligence algorithms, configured to be implemented through the computing device, platform, and server. It should be appreciated that additional algorithms not based on artificial intelligence can be incorporated and utilized.

As shown, the computing device 205 can be a virtual reality device 213, or can be any other computing device, such as tablet, phone, computer, or the like.

As shown, the user 209 can interact with the platform 207 such that the user provides their needs and/or desires 215 into the platform 207. As will be discussed, the user can provide their needs or desires through voice input, video input, or text input, wherein the one or more algorithms 211 are configured to receive and analyze the input.

It should be appreciated that the needs and/or desires can be anything that the user wants assistance with, such as an emotional need including help with anxiety, help with depression, help with grief, and help with particular situations. It should be appreciated that the system is not limited to a specific user need, but rather is designed to assist the user with any mental or performance assistance that they desire.

The platform 207, along with the software rules and server, are configured to create a meditation packet 217 to be provided back to the user 209, wherein the meditation packet provides for the user with tasks, help, and feedback based on the input needs/desires. It should be appreciated that the meditation packet can include any number of elements, including one or more of a question, an answer, a koan, poetry, a verse, a joke, a friend message, a mindset boost, insight activity, a podcast, motivation, performance preparation, music, scripture, humor, a voiceover, an audio book, a video, entertainment, creativity, conversations, programs, sequences of content, mood shifts, whispering, soundscapes, noises (e.g., city noise), affirmations, sleep talks, stories, education, sexual content, therapy, counseling, chanting, rituals, live content, and grief support.

System 201 can further include a user assessment feature 206, wherein the user has the ability to activate objective and/or subjective assessment of their experience. It should be appreciated that this feature is implemented through the computing device, wherein further data is collected from the user. The data allowing for assessment, including validated psychological assessments, opinion solicitation, raising of relevant questions, biomarkers, and physiological markers, including data collected from one or more sensors 208, such data including electroencephalogram (EEG), eye-movement (EM), photoplethysmogram (PPG), electrodermal activity (EDA), skin temperature (SKT). heart-rate variability (HRV), PPG peak interval, skin conductance (SC), and autonomic nervous system ANS activity and other marker(s). The data collected can be used to inform, or combined to inform, the guidance of the user's subsequent experiences, or enables a user to select, order, and create multimedia content to produce a flow of information that when experienced may amplify the user's experience of a selected emotion, mood, affect, concept, or desire. This additional assessment feature is designed to provide real-time and/or automated guidance to the user's experience.

It should be appreciated that the system 201 further includes a crowdsourced feature 219, wherein there are a plurality of secondary users, wherein the secondary users are providing needs and/or desires 221 as well as solutions 223. It should be appreciated that this creates data for the software rules to create the meditation packet 217. This provides for information that the user 209 can receive and utilize as needed to improve their emotional state.

It should be appreciated that the use of a crowdsourced feature 219 provides for a network effect that enables delivery of meditation packets that are personalized to the user's current need, and in turn, produces sequences of content that can be empirically test, and when successful, converted into prescription digital therapeutics. The collection of feedback from secondary users will provide the necessary data for the platform to continuously improve the meditation packets along with blending the user solutions and feedback with meditation and health content from professional sources.

It should be appreciated that in one embodiment of the present invention, the system and method are configured to strategically nurture positive emotions and/or mindsets with audio and visual input and has the effect of positively impacting a repetitive user's average emotional and/or physical experience, and/or reported emotional and/or physical state.

As shown in FIG. 2, system 201 can further include a social network application 225 as accessible and produced through the platform 207, wherein the social network application 225 provides for an online community of users that can engage and communicate around overall wellness of the users. The social network application 225 will create data 227 for use within the platform/algorithm(s)/server communication to aid in providing content for helping the users with their mental health challenges.

Figure 3:
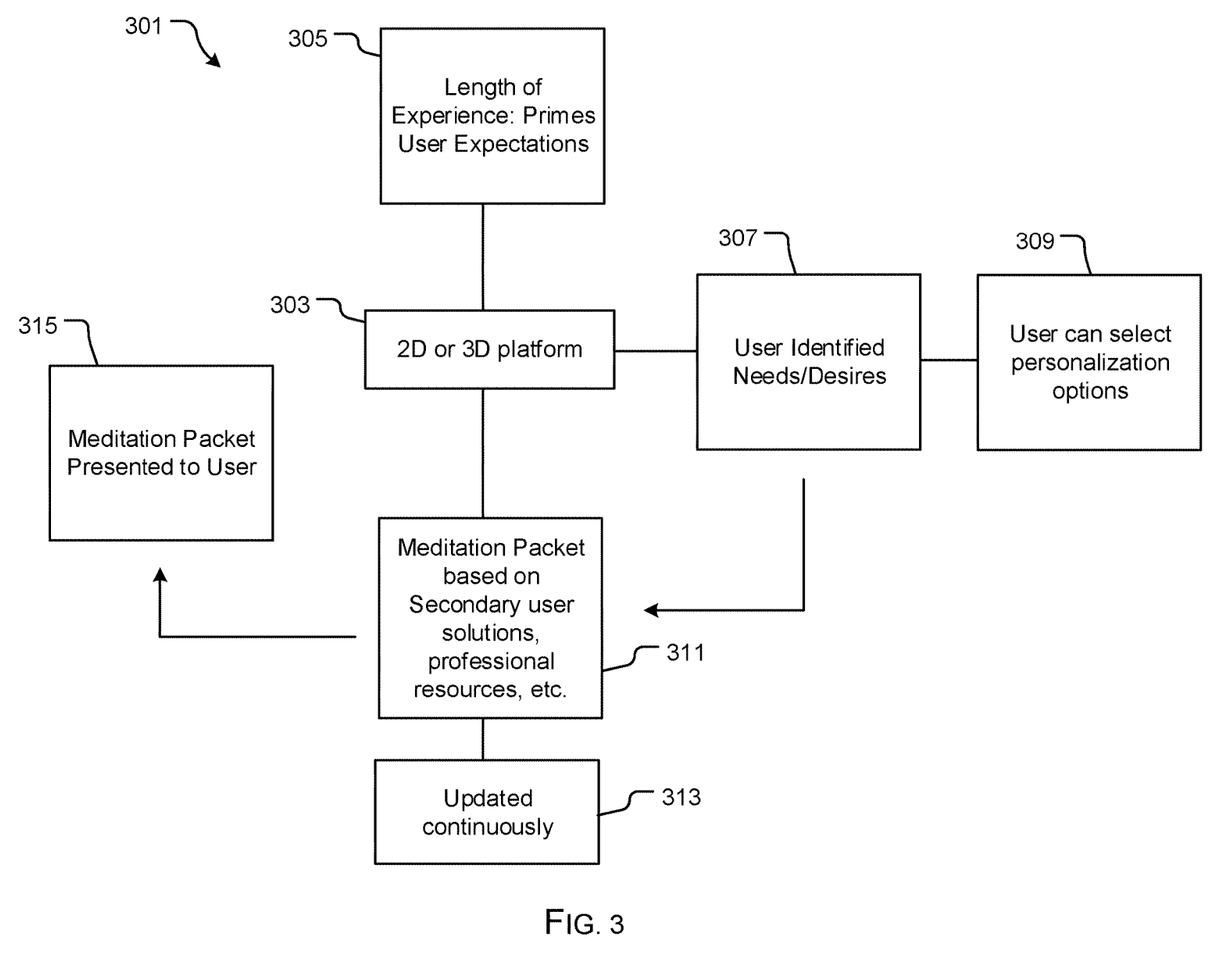
FIG. 3 is a simple schematic of a method associated with the system of FIG. 2.

In FIG. 3, a flowchart 301 depicts the steps associated with the method and system of the present invention. It should be appreciated that this system/method can be presented to the user through a 2D platform or a 3D platform, 303.

First, the user can select a length of experience that they would like 305 through the platform. This step primes the user for engaging in the experience for the selected time and sets the user's expectations for the experience. This helps to ensure that the user will successfully engage to completion of the experience.

The second step involves the user indicating their desires and needs 307. For example, the user may indicate that they desire to relax, wherein this information is utilized by the rule-based algorithm of the system while creating an experience for the user.

In some embodiments, the user can select and input additional user customization 309 to further customize their experience with the system. The user may select previous experiences based on previous visits, may select custom data features, such as music/video/audio/text, or a variety of other personalization options. This feature helps ensure that the user gets the most out of their experience. Further, the system is configured to objectively assess the user's emotional state to inform the meditation packet delivered and to adjust the one or more algorithms.

After the user makes their selections, a meditation packet for the user is compiled based on the selections 311 and based on data analyzed through the one or more software rules. It should be appreciated that in some embodiments, the user can bypass all of the customization and merely select a previous experience. The system can further be configured to continuously update and improve the meditation packets, 313, based on new data and improved algorithm learning features.

Figure 4:
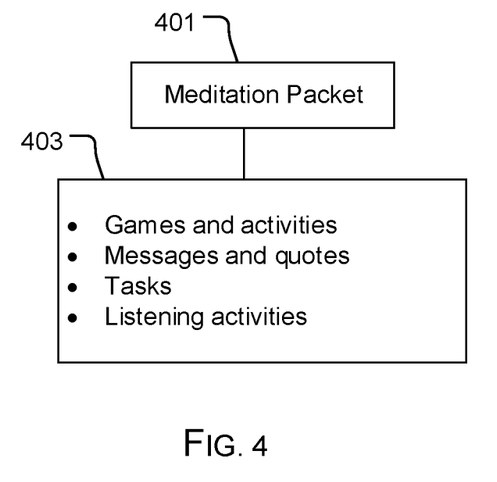
FIG. 4 is an example of elements included in a meditation packet in accordance with the present invention.

The meditation packet is then presented to the user 315. As shown in FIG. 4, it should be appreciated that meditation packet 401 can include various elements, including but not limited to, games and activities, messages and quotes, tasks, and listening activities, as shown with box 403

It should be appreciated and understood that the system can be adapted for a plurality of other embodiments, for example:

In one embodiment, the system provides an attention training system that enables the user to set his or her attention focus intention, the quality of which can in turn be measured and tracked during his or her experience of presented data and provided to the user as feedback following his or her data consumption experience. Repeated use of this training system improves the user's capacity for intentionally directed attention, a known correlate of mood regulation.

In another embodiment, the system enables a user to select and save a portion of any media content (e.g., from video, audiobooks, etc.) to the user's account so that it becomes available to the user for inserting into any future media at the user's, and or, the technology's election, thus personalizing the user's experience in the service of facilitating positive average mood change or maintenance with repeated exposure.

In another embodiment, the system enables clips from any content to be easily shared, (e.g., bible quotes, audio book clips from out of copyright or licensed books/audiobooks). In this way, the embodiment facilitates the mixing of spoken-word samples with other audio-video-vr samples to create new types of mixed media, and or, new social networks. Further, entire experiences can be shared as desired. The sharing feature allows for a user to share something with another user that the first user found to be helpful in shifting their mindset.

In another embodiment, the system pairs an algorithm that maps a learning goal(s) to content, and or, sequences of content, with measurement tools that facilitate performance tracking and feedback. For example, a learning goal of 'improve my flow state' could be mapped to a content category such as 'insight activities'. In this example, the training tool could be a system that presents alerts during content playback (such as the ringing of a bell) paired with a user prompt to rate current flow state experience. Similar training tools mapping learning goals to content sequences are possible for a wide range of learning goals, including personal development, reducing anxiety, feeling happy. etc.

In another embodiment, the system offers rewards for completing experiences or sequences of experiences, (perhaps based on user-goal-setting, and or, user's health provider recommendations, which informs an algorithm's selection of playback data).

In some embodiments, it is specifically contemplated that the system and method can facilitate the sharing of wisdom between generations as that sharing relates to applications in long term care facilities and would have the effect of improving the health and well-being both of the individual who shares as well as the health and well-being of the individual who is receiving and experiencing what was shared.

It should be appreciated and understood that the features of all contemplated embodiments can be combined, changed, or the like to create new embodiments.

Figure 5:
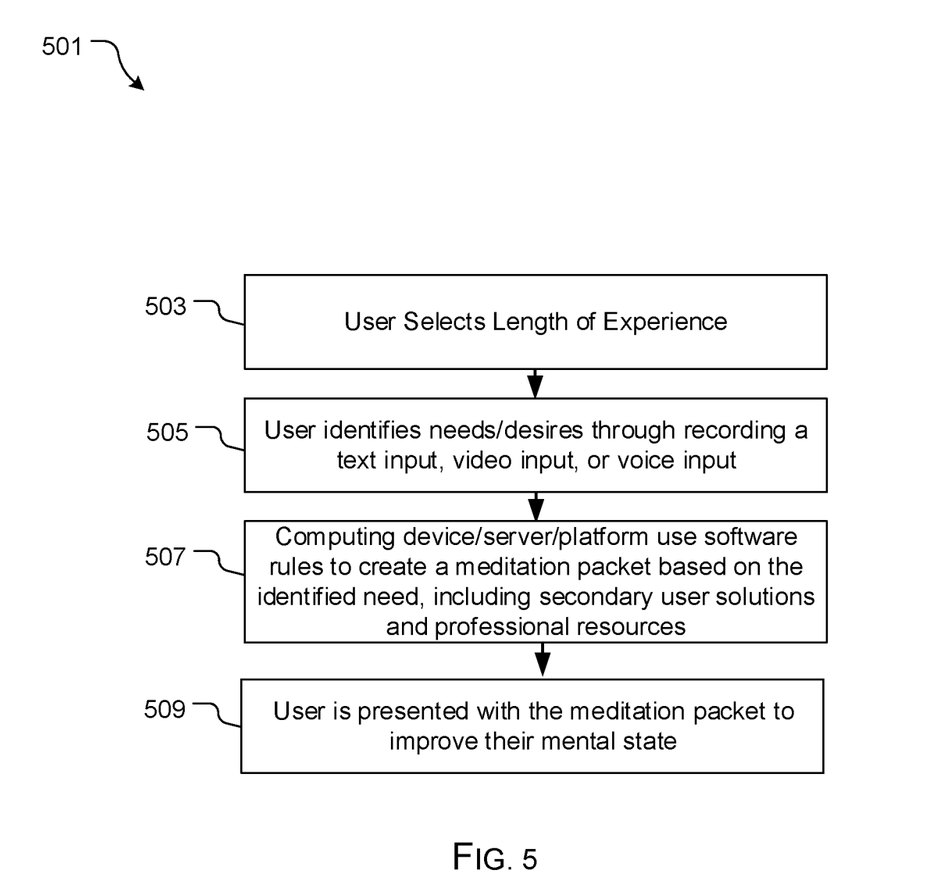
FIG. 5 is a flowchart of a method associated with the present invention.

In FIG. 5, a flowchart 501, further reiterates the method associated with system 201. During use, the user may select a length of experience, as shown with box 503. The user will then identify needs and/or desires through recording a text input, audio input, video input, or any other input, such as haptics and scents, as shown with box 505. The hardware and software components then use one or more algorithms to create a suitable meditation packet based on secondary user solutions as well as professional resources, as shown with box 507. The user is then presented with the meditation packet to improve their mental or emotional state, as shown with box 509.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system for improving an emotional mindset of a person, the system comprising:
    a server to receive and process data;
    a computing device in data communication with the server;
    one or more software rules implemented through the server and computing device;
    a crowdsourced connection to provide communication between the server and a plurality of secondary users, wherein the plurality of secondary users input user needs and user solutions, which create crowdsourced data to be processed and used by the one or more software rules, the crowdsourced data includes data regarding tested solutions and effectiveness of the tested solutions for one or more mindset needs, based on information collected from the plurality of secondary users;
    a platform implemented through the computing device, the platform performs the steps of:
        receive a user identified need, the user identified need being a mental or performance need that the user desires;
        determine two or more contents applicable to the user identified need; and
        output a meditation packet with the two or more contents to the user, wherein the user interacting with the meditation packet aids in alleviating the user identified need;
    the meditation packet created by the computing device, server, and one or more software rules, the meditation packet having the two or more contents, the two or more contents compiled based on correlating the user identified need to at least two separate sources of data, the at least two separate sources of data including:
        a first source being the crowdsourced connection; and
        a second source being obtained from a professional resource;
        wherein the first source is obtained through the crowdsourced connection and provides for data related to content that has been tested by at least one of the secondary users;
    wherein the platform analyzes the at least two separate sources of data to provide content that takes into account both secondary user solutions and feedback along with meditation and health content from professional sources;
    wherein the meditation packet is provided to the user through the platform; and
    wherein the one or more software rules utilize the data obtained by the platform to objectively assess effectiveness of the meditation packet and update subsequent meditation packets over time, when the data obtained by the platform indicates said update would benefit the subsequent meditation packets.

2. The system of claim 1, wherein the platform is further configured to: receive a user designated length of experience.

3. The system of claim 1, wherein the platform is further configured to: receive a user input solution associated with a need.

4. The system of claim 1, wherein the platform being configured to receive the user identified need is achieved through use of one or more of a text input, a video input, and a voice input.

5. The system of claim 1, wherein the computing device is a virtual reality device.

6. The system of claim 1, further comprising:
a social media application in data communication with the platform, server, and one or more software rules; and
data collected through user interaction with the social media application;
wherein the user and the plurality of secondary users can interact through the social media application to share experiences; and
wherein the data is used by the one or more software rules to aid in create the meditation packet and other content.

7. The system of claim 1, wherein the one or more software rules are artificial intelligence algorithms.

8. The system of claim 1, wherein the computing device is an augmented reality device.

9. The system of claim 1, further comprising:
a user assessment feature implemented through the computing device, the user assessment feature implemented through the platform to analyze data obtained from user interaction with the computing device and from one or more sensors, wherein the data is used to provide the user with an assessment of an experience with the platform, the data obtained from the one or more sensors including at least one of an electroencephalogram (EEG) data, eye-movement (EM) data, photoplethysmogram (PPG) data, electrodermal activity (EDA) data, skin temperature (SKT) data, heart-rate variability (HRV) data, PPG peak interval data, skin conductance (SC) data, and autonomic nervous system ANS activity.

10. A method for improving an emotional mindset of a person, the method comprising:
providing a platform to a user through a computing device, the platform and computing device being configured to implement one or more software rules with a server;
creating a crowdsourced connection between the server and a plurality of secondary users, wherein the plurality of secondary users input needs and solutions which create crowdsourced data to be processed and used by the one or more software rules, the crowdsourced data includes data regarding tested solutions and effectiveness of the tested solutions for one or more mindset needs based on information collected from the plurality of secondary users;
receiving a user identified need through the platform, the user identified need being a mental or performance need that the user desires;
determining two or more contents applicable to the user identified need through implementation of the one or more software rules;
creating a meditation packet to alleviate the user identified need, the meditation packet having the two or more contents, the two or more contents compiled based on correlating the user identified need to at least two separate sources of data, the at least two separate sources of data including a first source being the crowdsource connection and a second source being obtained from a professional resource,
outputting the meditation packet to the user thorough the platform, such that the user interacting with the meditation packet aids in alleviates the user identified need;
objectively assessing the meditation packet; and
updating subsequent meditation packets over time, when the objective assessment determines an update would benefit the subsequent meditation packets.

11. The method of claim 10, further comprising:
receiving a user designated length of experience; and
providing the meditation packet for the length of experience.

12. The method of claim 10, further comprising:
receiving a user solution associated with a need through the platform.

13. The method of claim 10, wherein the user identified need is received through one or more of a video input, a text input, and a voice input.

14. The method of claim 10, wherein the computing device is a virtual reality device.

15. The method of claim 10, further comprising:
providing a social media application in data communication with the platform, server, and one or more software rules;
collecting data from user interaction with the social media application; and
using the data for content creation
wherein the user and the plurality of secondary users can interact through the social media application to share experiences.

16. The method of claim 10, further comprising:
providing the user with an assessment of an experience with the platform, the assessment being based on collecting data from the user interaction with the computing device and platform.

* * * * *